United States Patent [19]

Fivez et al.

[11] Patent Number: 5,493,601
[45] Date of Patent: Feb. 20, 1996

[54] RADIOGRAPHIC CALIBRATION PHANTOM

[75] Inventors: Christiaan Fivez, Antwerp; Pieter Vuylsteke, Mortsel, both of Belgium

[73] Assignee: Agfa-Gevaert, Mortsel, Belgium

[21] Appl. No.: 347,825

[22] Filed: Dec. 1, 1994

[30] Foreign Application Priority Data

Dec. 24, 1993 [EP] European Pat. Off. .............. 93203671

[51] Int. Cl.$^6$ .................................................. G01D 18/00
[52] U.S. Cl. ............................................. 378/207; 378/18
[58] Field of Search ............................. 378/18, 56, 204, 378/207, 162

[56] References Cited

U.S. PATENT DOCUMENTS

| | | | |
|---|---|---|---|
| 2,356,358 | 8/1944 | Schneeman | 375/58 X |
| 4,280,047 | 7/1981 | Enos | 378/207 X |
| 4,352,020 | 9/1982 | Hariba et al. | 378/207 X |
| 4,460,832 | 7/1984 | Bighem | 378/207 X |
| 4,873,707 | 10/1989 | Robertson | 378/207 X |
| 4,980,904 | 12/1990 | Sones et al. | 378/207 |
| 4,985,906 | 1/1991 | Arnold | 378/207 X |
| 5,056,130 | 10/1991 | Engel | 378/207 |

*Primary Examiner*—David P. Porta
*Attorney, Agent, or Firm*—Richard J. Birch

[57] ABSTRACT

A phantom for determining attenuation by a combination of materials of polychromatic X-rays comprises a number of tubes that can be positioned in between a source emitting said X-rays and an X-ray detector. The tubes are held in a position so that they are directed towards the position of a source of radiation. In each tube a combination of thicknesses of said materials is provided.

9 Claims, 4 Drawing Sheets

| TUBE NUMBER | TUBE LENGTH(mm) | ALUM.(mm) | POLYCARB.(mm) |
|---|---|---|---|
| 1 | 241 | 25,0 | 216 |
| 2 | 238 | 21,7 | 216 |
| 3 | 232 | 15,9 | 216 |
| 4 | 225 | 9,2 | 216 |
| 5 | 219 | 3,4 | 216 |
| 6 | 216 | 0,0 | 216 |
| 7 | 211 | 25,0 | 186 |
| 8 | 208 | 21,7 | 186 |
| 9 | 202 | 15,9 | 186 |
| 10 | 195 | 9,2 | 186 |
| 11 | 189 | 3,4 | 186 |
| 12 | 186 | 0,0 | 186 |
| 13 | 169 | 25,0 | 144 |
| 14 | 166 | 21,7 | 144 |
| 15 | 160 | 15,9 | 144 |
| 16 | 153 | 9,2 | 144 |
| 17 | 147 | 3,4 | 144 |
| 18 | 144 | 0,0 | 144 |
| 19 | 120 | 25,0 | 83 |
| 20 | 120 | 21,7 | 83 |
| 21 | 120 | 15,9 | 83 |
| 22 | 120 | 9,2 | 83 |
| 23 | 120 | 3,4 | 83 |
| 24 | 120 | 0,0 | 83 |
| 25 | 120 | 25,0 | 31 |
| 26 | 120 | 21,7 | 31 |
| 27 | 120 | 15,9 | 31 |
| 28 | 120 | 9,2 | 31 |
| 29 | 120 | 3,4 | 31 |
| 30 | 120 | 0,0 | 31 |
| 31 | 30 | 25,0 | 0 |
| 32 | 30 | 21,7 | 0 |
| 33 | 30 | 15,9 | 0 |
| 34 | 20 | 9,2 | 0 |
| 35 | 10 | 3,4 | 0 |
| 36 | 5 | 0,0 | 0 |

FIG. 3

RADIOGRAPHIC CALIBRATION PHANTOM

DESCRIPTION

1. Field of the Invention

The present invention relates to a phantom for determining attenuation of polychromatic X-rays by a combination of materials.

2. Description of the Prior Art

When an object is positioned in a radiation beam emitted by a source of penetrating radiation, such as X-rays, the radiation beam is attenuated by the object.

In case monochromatic X-radiation is absorbed by a known homogenous material, the relation between the attenuation T of X-rays by said material and the thickness D of the material is given by the following equation:

$$T=-ln(N(E)/N_O(E))=\mu(E).D,$$

wherein $\mu(E)$ is the linear attenuation coefficient of the material and $N_O(E)$ is the number of photons of energy E before attenuation and $N(E)$ is the number of photons of energy E after attenuation.

If monochromatic X-radiation is successively attenuated by a sequence of materials, then the total attenuation by said sequence of materials is equal to the sum of the attenuation by the materials individually.

This is not correct for polychromatic X-radiation. In case of an X-ray beam of a non-constant spectrum, the attenuation factor can be different in different locations of an object of a homogenous material as a consequence of different absorption of different wave lengths.

In case of polychromatic irradiation the relation between attenuation T and material thickness D is not linear and the attenuation of the radiation by a number of materials is not equal to the sum of the attenuations by the materials individually.

When the attenuation of polychromatic X-rays by a number of materials is to be assessed, and the spectrum of the emitted radiation is unknown, it is not possible to calculate said attenuation by a combination of materials.

In this case, the attenuation is determined experimentally by exposing a phantom to X-rays emitted by a X-radiation source and by detecting the attenuated radiation.

In the state of the art phantoms for measurement of attenuation of polychromatic X-rays by a combination of materials (e.g. 2 materials) exist. These phantoms commonly consist of a combination of (two) step wedges, one of each material, said wedges being positioned so that combinations are formed of a larger thicknesses of a first material combined with a smaller thicknesses of a second material and visa versa.

This kind of wedges is not flexible and does not permit accurate measurement, for example because the distance towards the source of irradiation is not constant for every location in an element of the step wedge.

The state of the art phantoms do not have provisions for determining and eliminating radiation scatter.

OBJECT OF THE PRESENT INVENTION

It is an object of the present invention to provide a phantom for accurately determining the attenuation of polychromatic X-radiation by a combination of at least two materials.

It is a further object to provide such a phantom that can be applied for different combinations of materials in a flexible way.

It is still a further object of this invention to provide a phantom that allows for elimination of radiation scatter.

Further objects will become apparent from the description hereafter.

STATEMENT OF THE INVENTION

The objects of the present invention are achieved by providing a calibration phantom for determining the attenuation by a combination of at least two materials of polychromatic X-rays emitted by an X-ray source, comprising (a) a number of tubes that can be positioned in between said source and a X-ray detector, (b) means for holding said tubes in a position so that their axes are directed towards the position of said source, (c) in each of said tubes a combination of samples of known thickness of said materials.

For determining attenuation of polychromatic radiation by a combination of materials, the following procedure is applied:

first an X-ray detector, most conveniently an area detector such as a photostimulable phosphor screen is exposed to said polychromatic X-radiation in the absence of the phantom, next, an X-ray image of the phantom is generated by positioning the phantom in between the source of X-rays and the area detector and by exposing the phantom to the same amount and same spectrum of X-rays;

then, for each combination of materials in the phantom the radiation intensity $I_o$ in absence of the phantom and the radiation intensity $I_t$ attenuated by the phantom is measured, finally for each combination of materials the attenuation T is calculated in accordance with the following equation:

$$T=-ln(I_t/I_o).$$

The above method does not yet include elimination of radiation scatter. A specific embodiment of the phantom of the present invention that allows elimination of radiation scatter is disclosed furtheron.

A phantom in accordance with the present invention can be used for determining the attenuation by any combination of materials.

This phantom is very advantageous in case attenuation of polychromatic X-radiation by a human body material is to be determined. Since it is not feasible to subject the human body material itself to X-radiation for the purpose of determining attenuation properties, a method has been developed that is based on the following knowledge published by Alvarez R. and Macovski A. in Phys. Med. Biology, 1976, Vol. 21, No 5, 733–744 and entitled: "Energy-selective reconstruction in X-ray computerized tomography". The following has been disclosed.

For a certain group of materials, as for all the organic materials in a human body, and for the range of photon energies used in diagnostic radiology, the X-ray attenuation properties of every thickness combination of materials can approximately be represented by the attenuation properties of a combination of two equivalent thicknesses of two chosen basis materials. Basis materials are materials that have such characteristics that the attenuation properties of an organic material in the human body can be deduced from the attenuation caused by a combination of such basis materials. Examples are aluminum, polycarbonate . . .

The attenuation of radiation emitted by a source of polychromatic radiation can then be determined by exposing a number of combinations of known thicknesses of such basis materials to the radiation emitted by said source and by measuring the attenuated radiation.

The inventor has developed an embodiment of the method for generating a scatter-compensated radiation image in case of an exposure of an object by means of an irradiation source emitting polychromatic irradiation. The method has been described extensively in the European patent application 93203671.8 filed Dec. 24, 1993. The method makes use of calibration data representing the attenuation of the spectrum of said source that are generated by making use of combinations of thicknesses of different basis materials.

Such calibration data are preferably obtained by exposing a phantom according to the present invention, the combination of materials for which the attenuation is determined being basis materials.

For medical applications the materials are chosen to be a soft tissue equivalent and a bone equivalent material such as polycarbonate and aluminum respectively.

For reasons of convenience in the following the X-ray source is considered to be positioned above the phantom. The X-ray detector is then positioned under the phantom.

It will be clear that other arrangements are possible as long as these arrangements provide that X-rays emitted by the X-ray source are attenuated by the considered combination of materials and that X-rays attenuated by said combination of materials are detected by the X-ray detector.

In one embodiment of the phantom of the present invention each of said tubes is provided with a radiation beam stop that is located above the material that is positioned closest to the source of irradiation so that it covers part of said material from being exposed to X-rays.

Most conveniently this radiation beam stop is in the form of a piece of lead material that is positioned on top of one of the materials of the combination that is positioned in said tube most closely to the position of the source of irradiation.

Alternative embodiments can be used. For example an additional plate that is locally provided with a lead coating can be placed above the tubes.

The beam stops enable to determine the amount of scattered radiation and to eliminate the radiation scatter for the attenuation values.

For a given combination of materials provided in a tube, a detector will detect a certain amount of scatter radiation. By providing a beam stop on top of the material that is most close to the source of radiation, no direct (or primary radiation) is detected by the detector in the shadow of the beam stop.

If the diameter of the beam stop is small and the diameter of the samples of material is larger than the diameter of the beam stops, then the amount of scatter radiation detected in the shadow of the beam stop is approximately equal to the amount of scatter radiation detected in the vicinity of the beam stop.

The amount of radiation is detected in measurement locations in a ring surrounding the shadow of the beam stop and in the shadow of the beam stop. By subtracting from a first signal representing the radiation detected in said ring a second signal representing the radiation in the shadow of the beam stop, the scatter-free radiation amount is obtained.

In one embodiment the means for holding the tubes comprise a first plate having provisions for holding the tubes and the materials in the tubes so that the tubes are in a fixed position and the materials are held inside the tubes. It is required that the X-rays under and near the beam stop can fall onto a detector positioned under the phantom. So, these provisions must at least have a part positioned under said beam stop and near the beam stop that is transparent to X-rays. Preferably said platen has recesses having a collar to hold the tubes as well as the samples of material that are placed in the tubes.

A second plate having holes through which said tubes can be slided is provided. First and second plates are positioned relative to each other so that the tubes are directed towards the position of said source.

To eliminate the influence on the measurements of X-rays that would penetrate into the tubes through the walls of the tubes, the inner or the outer wall of the tubes are provided with a provision that prevents such penetration, for example a lead coating.

Detection of radiation by a detector on locations outside the tubes is prohibited by providing that at least one of said first or base plate and said second or support plate is opaque to X-rays in between the locations of the tubes so that X-radiation cannot reach a detector positioned under the phantom a-t locations in between tubes and hence cannot interfere with the radiation that has been attenuated by the combination of materials.

Preferably all of said tubes have a cylindrical shape and all of said tubes have an identical diameter and all of the samples of basis material have a cylindrical shape that fits into the tubes. This embodiment provides that the phantom is very stable (samples of material cannot move in the tubes) and the signal is cylindrical symmetrical so that a larger number of measurement points can more easily be chosen thereby enhancing the accuracy of the measurement.

It is further preferred that the support plate is displaceable so that the direction towards which the tubes point, can be changed. This enables that tubes are directed towards a source positioned at different distances from the detector.

BRIEF DESCRIPTION OF THE DRAWINGS

Further details concerning the phantom of the present invention are described hereafter with reference to the drawings wherein FIG. 3 is a table illustrating combinations of different thicknesses of basis materials.

DETAILED DESCRIPTION

A very interesting application is concerned with the assessment of the attenuation of polychromatic X-rays by organic materials in the human body.

As has already been described before, the X-ray attenuation properties of every thickness combination of materials can approximately be represented by the attenuation properties of a combination of two equivalent thicknesses of two chosen basis materials. Basis materials are materials that have such characteristics that the attenuation properties of an organic material in the human body can be deduced from the attenuation caused by a combination of such basis materials. Soft tissue and bone equivalent materials are e.g. polycarbonate and aluminum respectively.

The attenuation by human body material of radiation emitted by a source of polychromatic X-radiation can then be determined by exposing a number of combinations of known thicknesses of the above basis materials to the radiation emitted by said source and by measuring the attenuated radiation.

In this application it is advantageous to use a calibration phantom in accordance with the present invention since the calibration is to be performed very often and hence it would be highly time-consuming to perform an individual exposure to the radiation emitted by a polychromatic source of a great number of combinations of equivalent thicknesses of equivalent materials.

Figure 1:
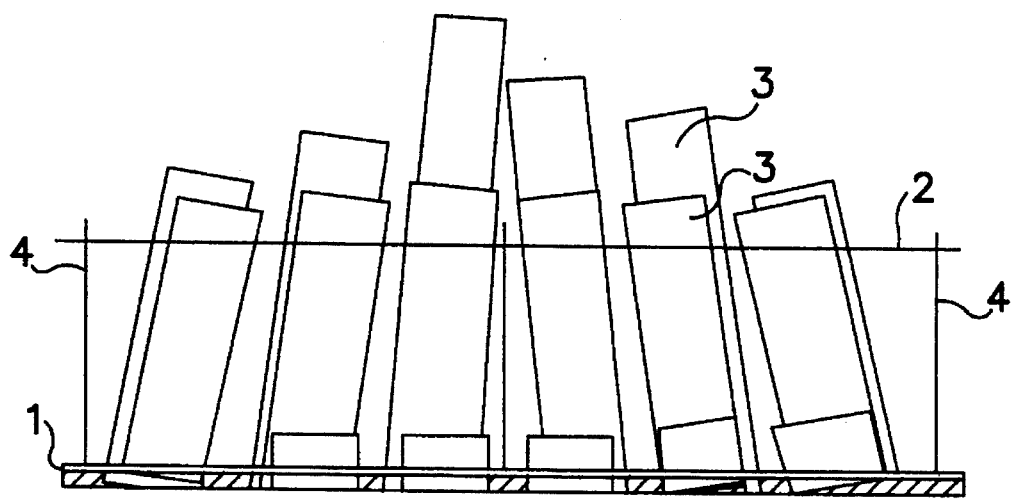
FIG. 1 is an embodiment of a calibration phantom according to the present invention.

A specific example of a phantom in accordance with the present invention that is used in this method comprises 36 cylindrical tubes, that are filled with a number of combinations of thicknesses of the basic materials aluminum and polycarbonate. The number of cylinders determines the number of combinations of basic materials for which the attenuation can be determined. This number is not limitative for the present invention. FIG. 1 is an illustration of such a phantom. The figure shows three (out of a total of 6) rows of cylindrical tubes positioned behind each other. The tubes have different heights. This is however not necessary as long it is provided that they can include different thicknesses of basis materials and that they can be directed towards the source of radiation.

FIG. 3 is a table giving for each tube, indicated by numerals 1 to 36 the height of the cylindrical tube and also the height (or thickness) of the included cylindrical samples of either of the materials.

The frame for holding the tubes and directing them with their axis pointing towards the radiation source consists of two parallel positioned plates.

A first so-called baseplate 1 has a number of recesses into which a number of cylindrical tubes 3 are placed.

The dimensions of the recesses are such that the tubes are supported, materials placed in the tubes do not slide through the tubes and if the tubes were not filled with the combination of materials for which the attenuation is to be determined, X-rays entering the tube at the upper side can reach a detector positioned under the tube.

Figure 2:
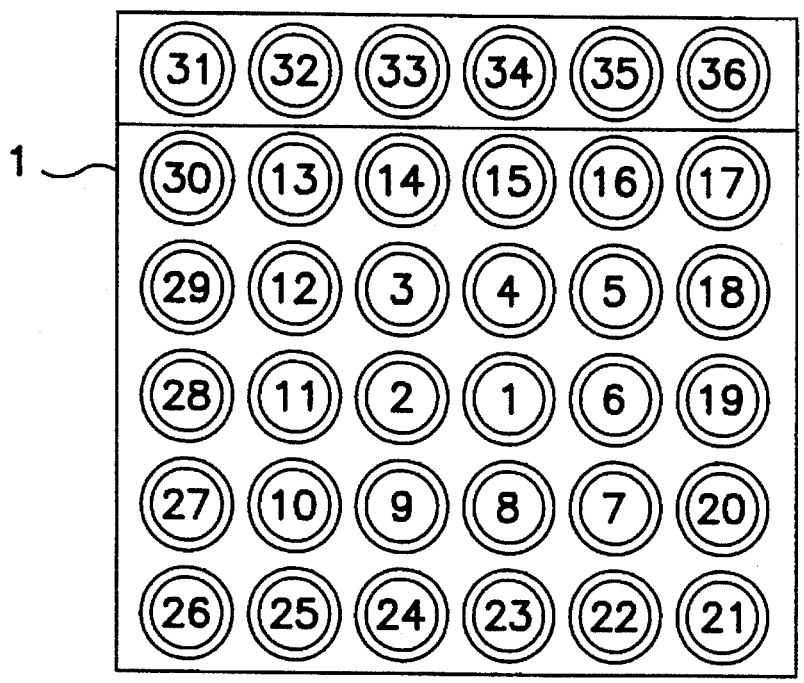
FIG. 2 shows a first or base plate.

The baseplate 1 is shown in FIG. 2, it is preferably a metallic plate provided with a lead layer in between the recesses so that X-rays cannot penetrate through the plate at locations in between the tubes and hence cannot expose the detector to scatter in between the tubes.

At a given distance above this plate, in this example this distance is equal to 12 cm, a second plate 2, referred to as supporting plate, is provided. The supporting plate has a number of holes through which the cylindrical tubes are slided. The position of the holes in the support plate together with the position of the support plate relative to the base plate provide that the cylindrical tubes are all directed with their axis towards a source of irradiation.

In one embodiment the cylindrical tubes were directed towards a single point located at a known distance, in this example 150 cm, measured above the center of the baseplate.

The supporting plate can be held above the baseplate by means of a fixed connection 4.

Alternatively the support plate is movable. A movable support plate is preferred in case calibration data are to be obtained for different positions of the radiation source relative to a detector, i.e. for a set of distances between a source of irradiation and a detector.

A movable support plate provides that the direction into which the cylindrical tubes point, can be changed hereby enabling that the tubes are directed towards a source of irradiation positioned at several distinct distances within a given range of distances.

Figure 4:
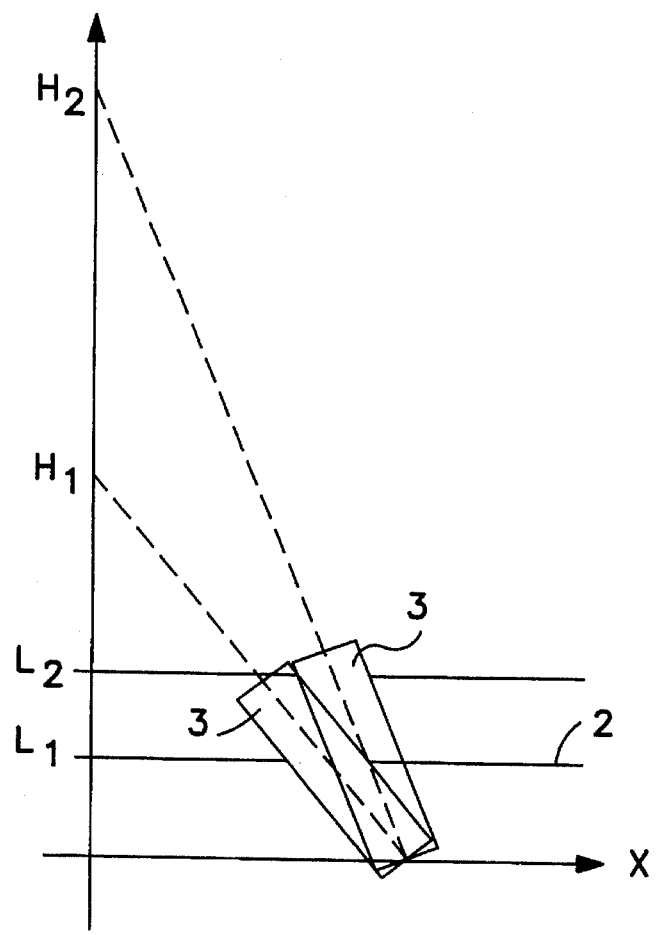
FIG. 4 illustrates the adjustment of the direction of the tubes.

The support plate can be fixed for a certain distance of the irradiation source relative to the frame and can be changed for other distances within the given range. This embodiment is illustrated in FIG. 4. $L_1$ and $L_2$ indicate the position of the support plate, $H_1$ and $H_2$ indicate the position of the X-rays source.

For example, when the distance between source of irradiation and detector is doubled, the distance between the base plate and the support plate is likewise to be doubled in order to have the cylindrical tubes point at the irradiation source.

Figure 5:
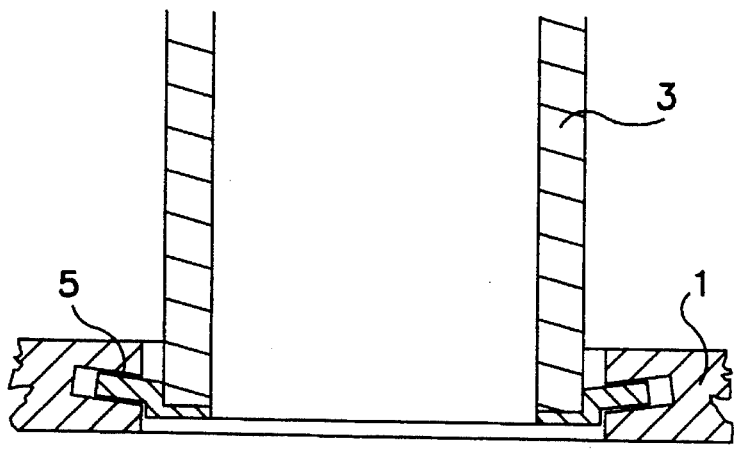
FIG. 5 illustrates the fixing of the tubes into the base plate.
Figure 6A:
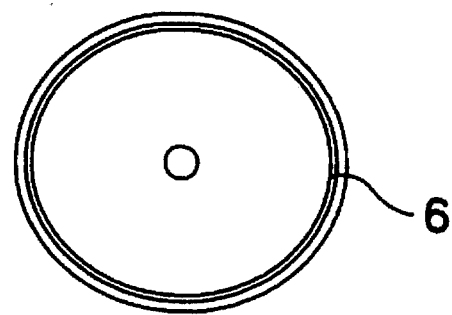
FIG. 6 is an illustration of a tube filled with two basis materials.
Figure 6B:
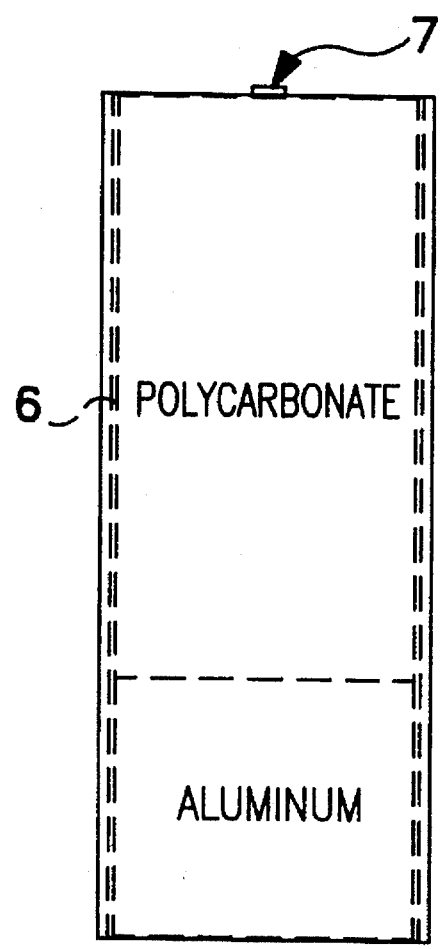

The change of the angle between the base plate and the axis of the cylindrical tubes that are farest away from the center of the base plate which occurs due to the displacement of the support plate, is relatively small. The change of the diameter of the openings in the support plate which is required when changing the distance between base plate and support plate is consequently also relatively small and can be bridged by a non-rigid fixing of the tubes in the base plate. This non-rigid fixing can for example be realised by means of an elastically deformable substance 5 positioned in the recessed in the base plate in between the tubes 3 and the base plate 1 as is shown in FIG. 5.

The inner wall of the tubes is preferably provided with a lead layer 6 so that scattered radiation cannot penetrate through the walls inside the tubes.

Also on top of the upper material in the tubes, i.e. the material that faces the source of irradiation a lead beam stop 7 is provided, said beam stop only covering part of the upper surface of the upper material. This lead beam stop provides a measurement of the scattered radiation under the beam stop.

Indeed, since in this application one is only interested in the attenuation by X-rays by a combination of thicknesses of basic materials, the influence of scattered radiation is to be eliminated. For this purpose, a cylindrical lead beam stop is provided in the center of the surface of the upper basic material in each cylindrical tube.

The procedure for determining attenuation of polychromatic X-radiation by the combination of thicknesses of basis materials provided in the tubes of the phantom is as follows.

First a radiation image is generated representing un-attenuated X-radiation emitted by a source of radiation. This radiation is performed by exposing an area detector such as a photostimulable phosphor screen to the radiation emitted by said source without any object or phantom being positioned in the beam of radiation.

Next, the phantom is exposed under the same exposure conditions as used when generating the un-attenuated X-ray image.

Then both radiation images are read by stimulating the photostimulable phosphor screens with stimulating irradiation of the appropriate wavelength, by detecting light emitted upon stimulation and by converting the detected light into a signal representation.

The signal representation representing the un-attenuated image and the signal representation representing the phantom image are then combined to calculate attenuation values.

Preferably interpolation is applied to the data of the image representation of the phantom image.

An additional scatter signal can be obtained at the locations of said lead bodies.

To provide an accurate measurement it is necessary that the dimensions of the section of the tubes and of the samples of basic material is adequately large.

Preferably the diameter of all of the cylindrical tubes is identical. The basic materials are preferably provided in a cylindrical form having a diameter that is slightly smaller than the diameter of the tube so that the material fits very well inside the tube.

The tubes have been described as being cylindrical. It is evident that any elongate hollow container of whatever cross-sectional shape can be used as a tube as well. The basis materials included in the tubes are preferably but not necessarily of the same cross-sectional shape as the tubes.

We claim:

1. A calibration phantom for determining the attenuation of polychromatic X-rays emitted by an X-ray source by a combination of at least two materials, comprising
   (a) a number of tubes that can be positioned in between said source and a X-ray detector,
   (b) means for holding said tubes in a position so that their axes are directed towards the position of said source,
   (c) in each of said tubes a combination of samples of known thickness of said materials.

2. A phantom according to claim 1 wherein for each of said tubes a beam stop is provided above the piece of material that is positioned closest to said X-ray source so that said beam stop covers part of said material from being exposed to X-rays.

3. A phantom according to claim 1 wherein said means for holding the tubes comprise
   a first plate having provisions for holding said tubes and said materials, at least a part of said provisions being transparent to X-rays so that X-rays can be detected;
   a second plate having holes through which said tubes can be slid,
   first and second plate being relatively positioned so that the tubes are directed towards said source.

4. A phantom according to claim 1 wherein the side-walls of the tubes are provided with X-ray penetration prohibiting means.

5. A phantom according to claim 1 wherein means are provided to prevent X-ray detection by said detector in between said tubes.

6. A phantom according to claim 3 wherein at least one of said first plate and said second plate is opaque to X-rays in between said tubes.

7. A phantom according to claim 1 wherein all of said tubes have a cylindrical shape with an identical diameter and all of the samples of material have a cylindrical shape that fits into the tubes.

8. A phantom according to claim 3 wherein the distance between first and second plate is variable.

9. A phantom according to claim 8 wherein said second plate is displaceable.

* * * * *